United States Patent [19]
Beidler et al.

[11] Patent Number: 5,112,951
[45] Date of Patent: May 12, 1992

[54] SEPARATION OF ANTI-METAL CHELATE ANTIBODIES

[75] Inventors: Daniel E. Beidler, Poway; Rodney A. Jue, San Diego, both of Calif.

[73] Assignee: Hybritech Incorporated, San Diego, Calif.

[21] Appl. No.: 388,333

[22] Filed: Jul. 31, 1989

Related U.S. Application Data

[63] Continuation-in-part of Ser. No. 386,428, Jul. 28, 1989, abandoned.

[51] Int. Cl.$^5$ .......................... C07K 3/18; C07K 15/28
[52] U.S. Cl. ................... 530/387.3; 530/415; 530/417; 530/416; 530/388.9; 530/389.8
[58] Field of Search ................ 530/387, 416, 415, 417

[56] References Cited

U.S. PATENT DOCUMENTS

| | | | |
|---|---|---|---|
| 4,390,628 | 6/1983 | Johansen. | |
| 4,474,893 | 10/1984 | Reading. | |
| 4,606,825 | 8/1986 | Crane et al. | 530/387 |
| 4,634,586 | 1/1987 | Goodwin et al. | 424/1.1 |
| 4,722,892 | 2/1988 | Meares et al. | 435/7 |

OTHER PUBLICATIONS

Reardan et al., Antibodies Against Metal Chelates, Nature 316:265-268 (1985).
Fred E. Regnier, The Role of Protein Structure in Chromatographic Behavior, Science 238:319-323 (1987).
Haff et al., Use of Electrophoretic Titration Curves for Predicting Optimal Chromatographic Conditions for Fast Ion-Exchange Chromatography of Proteins, J. of Chromatography 266:409-425 (1983).
David R. Nau, Effects of Mobile Phase Conditions on Protein Confirmation and Chromatographic Selectivity in Ion Exchange and Hydrophobic Interaction Chromatography, BioChromatography 4:62-69 (1989).
H. Peeters, Protides of the Biological Fluids, Proceedings of the Thirtieth Colloquium, Pergamon Press (1982).
Charles W. Parker, Principles of Competitive Protein--Binding Assays, J. B. Lippincott Company, 25-56.
Scott et al., 1987, Biotechnology Progress 3(1): 49-56.
Parham et al., 1982, J. Immunol. Methods 53:133-173.
Osterman, L. A. 1986, *Methods of Protein and Nucleic Acid Research: Chromatography*, Springer Verlag, N.Y., pp. 226-267.

*Primary Examiner*—Margaret Moskowitz
*Assistant Examiner*—Keith C. Furman
*Attorney, Agent, or Firm*—June M. Bostich; Theresa A. Brown; Cathryn Campbell

[57] ABSTRACT

The present invention provides a method for the separation of anti-metal chelate antibodies from non-specific proteins, including antibodies, by applying a preparation containing the anti-metal chelate antibodies to an oxo acid derivatized solid support and eluting first with an elution buffer containing sufficient salt concentration to elute non-specific proteins but not sufficient to elute the anti-metal chelate antibodies and then increasing the salt concentration of the elution solution so as to elute the anti-metal chelate antibodies. In one embodiment, the oxo acid derivatized solid support is a sulfopropyl resin. Appropriate salts include sodium phosphate, sodium chloride and sodium acetate. The method can be used to separate monoclonal or polyclonal anti-metal chelate antibodies from non-specific proteins as well as to separate bifunctional anti-metal chelate antibodies from monoclonal anti-metal chelate antibodies and other non-specific proteins. The method is also useful for separating anti-metal chelate antibody fragments bearing antigen reactive regions from non-specific proteins.

24 Claims, 1 Drawing Sheet

SEPARATION OF ANTI-METAL CHELATE ANTIBODIES

BACKGROUND OF THE INVENTION

This application is a continuation-in-part of Ser. No. 07/386,428, filed Jul. 28, 1989, now abandoned.

This invention relates to methods of separating antibodies and, more specifically, to a method of separating anti-metal chelate antibodies from other antibodies and proteins.

The last twenty five years have witnessed a revolution in the field of immunology. During the 1970's methods were developed of producing in quantity single species of antibodies, the proteins which the immune system uses to recognize, bind and eventually eliminate substances which are recognized as foreign. In order to specifically bind to the enormous range of potential antigens, each of the some $10^5$ to $10^8$ lymphocyte lineages which an individual possesses produces different antibodies with specificity for a different foreign substance, or antigen. By fusing a single antibody-producing lymphocyte with an immortalized cell, such as a cancer cell, it is now possible to make a single lymphocyte clone, each cell producing the same monoclonal antibody. The development of such hybridomas to produce monoclonal antibodies has had an enormous impact on the ability to both diagnose and treat a vast array of diseases.

Antibodies comprise two identical pairs of a heavy and light peptide chain arranged in the shape of a "Y". Each of the arms contains a site which binds to the antigen through various non-covalent interactions, including ionic interactions, hydrogen bonding and van der Waals forces, which result in an affinity between the antibody and its cognate antigen. This antigen-binding site is encompassed within an antigen reactive region which corresponds to the so called variable region of the antibody. In native antibodies, both antigen reactive binding regions will be identical. "Bifunctional antibodies" have been produced which express two different variable regions. These bifunctional antibodies can be produced chemically or by engineered cells which simultaneously express two different sets of genes encoding the antibody proteins. These gene products then assemble into a variety of species of antibodies exhibiting different combinations of antibody gene products including two which exhibit identical antigen-binding sites ("monofunctional antibodies") and one exhibiting dissimilar antigen-binding sites.

Bifunctional antibodies have great utility in allowing simultaneous binding to more than one antigen. As one example of such use, a bifunctional antibody having one arm specific for an antigen expressed on the surface of a tumor cell and one arm specific for an imaging or therapeutic moiety may be effectively used to target such a moiety to the site of a tumor. Among the moieties so used for such therapeutic and diagnostic purposes are metals in metal chelates. Antibodies have binding affinity for metal chelates are termed "anti-metal chelate antibodies."

The recent developments of antibody technology have generated a need for methods to purify antibodies from proteins and other contaminants and to isolate specific species of antibodies from other antibodies. Conventionally, two methods have been used to separate antibodies: ion exchange chromatography and affinity chromatography. Ion exchange chromatography utilizes a solid support to which charged functional groups are covalently attached. The ionic interaction of these charged groups with charges available on the surface of various proteins provides a means of separating many types or families of protein. A protein whose surface is negatively charged will likely bind to an anion exchanger which has positively charged functional groups. While a protein whose surface exposes predominately positive charges will likely bind to a cation exchanger. The binding of these proteins is influenced by pH, salt composition and concentration and as such these parameters can be utilized to isolate antibodies as a family from other types of proteins. While ion exchange chromatography has proved quite useful in certain applications, it has the critical limitation that antibodies having similar physical characteristics but distinct functional characteristics, such as antigen binding, are usually not differentiated.

More specific purification can be achieved using an affinity column containing a resin to which is bound the cognate antigen or hapten of the antibody to be isolated. A hapten is a small molecule which is antigenic when attached to a carrier. The antibody preparation is passed over the column, with antibodies specific to the antigen binding to and being retained on the column. Because of the strength of the antigen-antibody binding, a solution containing the cognate is required to elute the antibody. Alternatively, other types of elutions are often harsh, such as extreme pH or the presence of chaotropic agents, which can denature the antibodies. Alternatively, a hapten analog having lesser affinity may be used in order to optimize the purification.

Despite its potential for separating antibodies with similar physical characteristics such affinity purification has certain serious drawbacks, however. For example, it may be difficult or impossible to separate the antibodies from the antigen or hapten with which they elute. In addition, the cognate and cognate-resin may be unavailable or costly. Even more importantly, the antibody may be denatured by the elution conditions.

There thus exists a need for an inexpensive and effective method for specifically isolating anti-metal chelate antibodies from non-specific antibodies or proteins which does not result in their being denatured during the process. Preferably, such a method should be effective in isolating polyclonal fractions enriched in anti-metal chelate antibodies as well as monoclonal antibodies and their bifunctional derivatives. The present invention satisfies these needs and provides related advantages as well.

SUMMARY OF THE INVENTION

The present invention provides a method for the separation of anti-metal chelate antibodies from non-specific proteins, including antibodies, by applying a preparation containing the anti-metal chelate antibodies to an oxo acid derivatized solid support and eluting first with an elution buffer containing sufficient salt concentration to elute non-specific proteins but not sufficient to elute the anti-metal chelate antibodies and then increasing the salt concentration of the elution solution so as to elute the anti-metal chelate antibodies. In one embodiment, the oxo acid derivatized solid support is a sulfopropyl resin. Appropriate salts include sodium phosphate, sodium chloride and sodium acetate. Alternatively, the anti-metal chelate antibody can be selectively eluted with a solution containing a metal chelate or analog thereof. The method can be used to separate monoclonal or polyclonal anti-metal chelate antibodies from non-specific proteins as well as to separate bifunctional anti-metal chelate antibodies from monoclonal anti-metal chelate antibodies and other non-specific proteins. The method is also useful for separating anti-metal chelate antibody fragments bearing antigen reactive regions from non-specific proteins.

DETAILED DESCRIPTION OF THE INVENTION

Figure 1A:
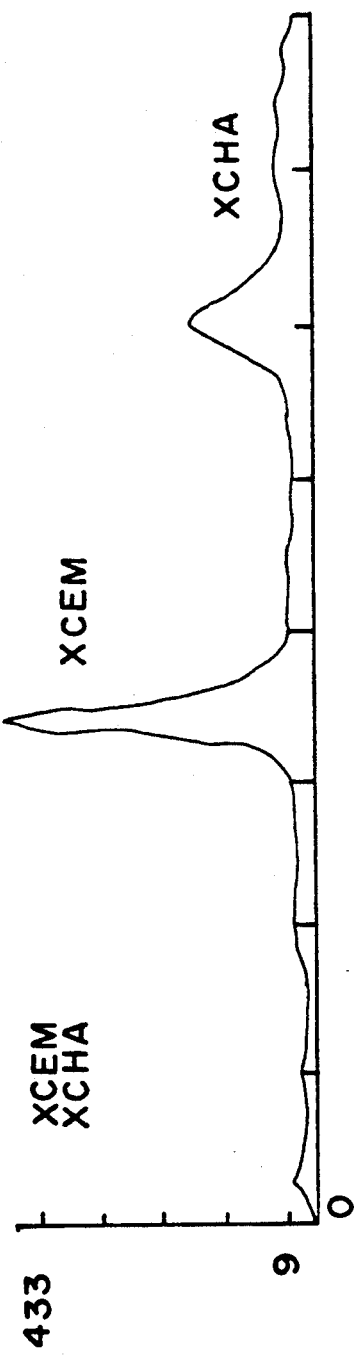
FIGS. 1a and 1b are graphs of ultraviolet absorbance at 283 nm over time showing the elution scan of an anti-metal chelate antibody (XCHA351) and a non-specific antibody (XCEM449.08) chromatographed as described in Example II, (1a) in the absence of solubilized hapten analog (Co/EDTA) and (1b) in the presence of solubilized hapten analog.

The present invention provides an effective method for separating anti-metal chelate antibodies from non-specific proteins, which may include other non-specific antibodies. The method exploits the unexpected ability of anti-metal chelate antibodies to bind to a non-cognate antigen, an oxo acid moiety, through their antigen reactive regions, thus differentiating them from other non-specific antibodies and proteins. While antigens and haptens, or their analogs such as derivatives and fragments, have been used on the solid phase of affinity columns, the present method is based on a binding between anti-metal chelate antibodies and a non-cognate hapten or analog through their antigen-binding site. It is, moreover, an advantage of the present invention that only an elevated salt concentration is needed to elute the anti-metal chelate antibodies. Alternatively, however, anti-metal chelate antibodies can be selectively eluted with a metal chelate or analog thereof. Further, no harsh or denaturing elution conditions, common to conventional affinity purification systems, are required.

The invention is premised on the unexpected ability of anti-metal chelate antibodies to bind to negatively charged multi-oxygen resonance structures in a manner which reflects their immunological specificity, indicating that the binding is with their antigen reactive region, at or near the antigen-binding site. In particular, anti-metal chelate antibodies exhibit attraction for oxo acids, which, as the term is used herein, include negatively charged, phosphorus- or sulfur-containing, multi-oxygen moieties. Examples of such oxo acids include sulfonate, sulfate, phosphonate, phosphate and phosphate moieties. Such oxo acids can be attached to a solid support, to form an oxo acid derivatized solid support. When such an oxo acid solid support is used as the solid phase in a chromatographic method, monoclonal anti-metal chelate antibodies can be separated from non-specific proteins and similarly polyclonal anti-metal chelate antibody enriched fractions can be obtained from antiserum.

In addition to distinguishing monoclonal and polyclonal anti-metal chelate antibodies from non-specific proteins, the invention permits the separation of bifunctional anti-metal chelate antibodies from monofunctional anti-metal chelate antibodies, such as would be found together in the culture fluid from a polydoma. The various species of antibodies in this culture fluid exhibit discrete retention times when eluted with an increasing salt concentration; the active bifunctional anti-metal chelate antibodies elute from the oxo acid derivatized solid support at a lower salt concentration than the active monofunctional antimetal chelate antibodies. This separation reflects the difference in avidity between a bifunctional antibody having a single anti-metal chelate binding site ("monovalent") and a monofunctional anti-metal chelate antibody having two antigen-binding sites ("bivalent"). Thus, the bifunctional anti-metal chelate antibodies can be effectively separated from the other, non-desired, species.

As used herein, the term "anti-metal chelate antibodies" refers to antibodies which have a high affinity for at least one metal chelate or metal chelate analog, generally greater than about $10^6$ L/M, preferably greater than $10^7$ L/M, most preferably greater than $10^8$ L/M. However, a particular anti-metal chelate antibody will, of course, exhibit differing affinities for different metal chelates. Antibodies not exhibiting such an affinity for metal chelate haptens are referred to as "non-specific antibodies." Non-specific antibodies together with non-antibody proteins are termed "non-specific proteins." For a description of anti-metal chelate antibodies see U.S. Pat. No. 4,722,892 and Reardan, et al., Nature 316:265–268 (1985), which are incorporated herein by reference. Metal chelates include any metal ion in the (II) or (III) oxidation state, including radioactive isotopes, complexed with a polycarboxylate chelating agent, including but not limited to EDTA, DTPA, and DOTA. For a list of such metals, see Reardan, supra. For a discussion of chelating agents see U.S. Pat. No. 4,678,667, which is incorporated herein by reference.

The method of the invention is also suited to the separation of anti-metal chelate antibody fragments which contain the antigen reactive region from non-specific proteins, including non-specific antibodies and their fragments. As used herein, the term anti-metal chelate antibodies includes fragments thereof which bear antigen reactive regions (Fab fragments including Fab; F(ab')$_2$ and Fab').

The method of the present invention has several advantages over more conventional affinity chromatography methods for the purification of anti-metal chelate antibodies. As indicated, not only does the method permit separation of anti-metal chelate antibodies from non-specific antibodies, but the method also permits the differentiation of antibodies having different avidity, by virtue of their valence, for the oxo acid derivatized solid phase support. In addition, it is more cost effective, as oxo acid derivatized solid phase supports, buffers and salts are less expensive and more readily available than metal chelate resins and metal chelate haptens. Also, the column can be easily sanitized, depyrogenated, cleaned of accumulated protein and regenerated, as by treatment with 0.2 N sodium hydroxide.

Anti-metal chelate monoclonal antibodies bind much more tightly to such an oxo acid derivatized solid support than do other proteins commonly found in tissue culture supernatants and, unexpectedly, bind even tighter than do non-specific monoclonal antibodies with higher pI's. The pI or "isoelectric point" of an individual protein or antibody is determined primarily by amino acid composition and is defined as the pH at which the net charge of that protein is zero. Above its isoelectric point, the protein has a net negative charge and below its isoelectric point, the protein has a net positive charge. At any given pH, a protein with a higher pI would be more positively charged, or conversely be less negatively charged, than a protein with a lower pI. Particularly among proteins with similar structure and physical characteristics, such as antibodies, a higher pI would be expected to predict stronger interaction with the negatively charged functional groups on an oxo acid derivatized solid support, as ionic forces generally account for the interaction of proteins with negatively charged functional groups. Yet, even among antibodies genetically engineered to have identical constant regions, the anti-metal chelate antibody will be retained longer on the oxo acid derivatized solid support than a non-metal chelate specific antibody having a higher pI.

As an indication that this behavior of anti-metal chelate antibodies on oxo acid derivatized solid supports exhibit immunologically specific binding, anti-metal chelate antibodies bearing the same antigen reactive binding region sequences, but having different constant regions and pI's, as in the case of chimeric antibodies and the native murine antibodies from which they were derived, exhibit the same extended retention time on the oxo acid derivatized solid support. These unexpected observations indicate that pI does not, in this case, explain the primary behavior of antibodies having a metal chelate specificity. Even more conclusively, the presence of a metal chelate hapten in solution-phase will effectively eliminate the anti-metal chelate antibodies' unexpectedly strong binding to the oxo acid derivatized solid phase by shortening their retention times so as to be comparable to those of non-specific antibodies. Considering the small size of these competing solution phase metal chelate haptens, the site of interaction which accounts for this unexpected binding behavior of anti-metal chelate antibodies must be near or identical with the antigen-binding site of these anti-metal chelate antibodies.

The unexpectedly strong oxo acid binding reaction and its abrogation in the presence of metal chelate haptens indicates that anti-metal chelate antibodies bind to oxo acid derivatized solid supports by a mechanism which is distinct from normal mechanisms of cation exchange chromatography and that this new mechanism of interaction is related to the immunological specificity of these antibodies. Moreover, this unexpected behavior extends to bifunctional antibodies derived from anti-metal chelate antibodies. Such bifunctional antibodies have only a single metal chelate binding site, and it is this monovalence which accounts for their being measurably less well retained on an oxo acid derivatized column than is the monofunctional anti-metal chelate antibody from which they were derived, which has two metal chelate hapten-binding sites.

The interaction between anti-metal chelate antibodies and the oxo acid derivatized solid support exhibits a behavior characteristic of immunologically specific binding and reflects an interaction at or near the antigen-specific binding site. However, the fact that only increasing salt concentration is required for their elution indicates that any affinity that these antibodies have for the oxo acid derivatized solid phase support is low in comparison to their affinity for the metal chelate. While not wishing to be bound by this explanation, oxo acid groups on the solid support may mimic the three dimensional spatial configuration or charge density pattern of a portion of the metal chelate hapten, thereby accounting for the antibody's affinity, albeit low, for the matrix. Such conformational similarity is plausible as the oxo acid derivatized solid support does possess oxygen atoms with negative charges like the metal chelate hapten. This characteristic indicates that other negatively charged multi-oxygen resonance structures would also be suitable derivatives for use in the method of the invention. Whatever the basis of this interaction, the behavior of anti-metal chelate antibodies on the oxo acid derivatized column can best be described as an interaction reflecting the antigen reactivity of the anti-metal chelate antibody.

Various anti-metal chelate antibodies are known or available. Examples include CHA255 and CHB235, which are monoclonal antibodies of murine origin which have particular affinity for an Indium-EDTA complex See U.S. Pat. No. 4,722,892. Anti-metal chelate antibodies and non-specific antibodies referred to herein are listed with their characteristics in Table I.

TABLE I

| Antibody | pI | specificity | characteristics |
|---|---|---|---|
| CHA255 | 7.5 | $^{111}$In metal chelate | murine monoclonal monofunctional |
| CHB235 | 6.6-7.2 | $^{111}$In metal chelate | murine monoclonal monofunctional |
| XCHA351 | 8.5 | $^{111}$In metal chelate | chimeric monoclonal monofunctional |
| XCEM449.08 | 8.8 | tumor CEA | chimeric monoclonal monofunctional |
| CYA339 | | $^{90}$Y metal chelate | murine monoclonal monofunctional |
| CEVMSC | 7.0-7.2 | tumor CEA | murine monoclonal monofunctional |
| ECH037 | | $^{114}$In metal chelate/tumor CEA | murine polydoma produced bifunctional |
| BxBFA | 8.6 | $^{111}$In metal chelate/tumor CEA | chimeric monoclonal bifunctional |
| pCYA | | Y-metal chelate | murine polyclonal monofunctional |

Both monoclonal and polyclonal anti-metal chelate antibodies can be made by methods known to those skilled in the art. For example, an antigen can be prepared by conjugating a chelating agent to a carrier in solution. The resulting solution is then mixed with a metal salt, such as indium citrate, and dialyzed. Alternatively, one could use gel filtration in place of dialysis. The amount of attached chelate can be determined from the absorbance or by radioactive titration. Hybridoma cells producing anti-metal chelate antibodies can be prepared by methods well known in the art. See, for example, ANTIBODIES, A LABORATORY MANUAL (Harlow and Lane, eds.) Cold Spring Harbor, New York (1988), which is incorporated herein by reference.

In the preparation of CHA255 and CHB235, for example, an indium-EDTA antigen was prepared. Keyhole limpet haemocyanin (9.3 mg) was allowed to react in 265 µL aqueous solution, pH 6.0, with (L)—SC—N—C$_6$H$_4$—CH$_2$—EDTA (isothiocyanate benzyl-EDTA; ITCBE) for eight hours at 36° C. The resulting solution was mixed with 90 µL of 0.1 M indium citrate and dialyzed against 1 mM EDTA, 0.15 M NaCl. From the absorbance of the thiourea group at 310 nm, it was determined that there was approximately 0.1 mg of attached chelate per mg of protein.

Spleen cells from BALB/c mice, multiply immunized with the antigen described above, were fused with a variant of the P3.653 myeloma cell line using the technique of Gerhard, *Monoclonal Antibodies*, (Kennett, et al., eds.) Plenum Press New York (1980), which is incorporated herein by reference. The resulting hybridomas were screened, using a solid phase second antibody radioimmunoassay, for their ability to bind In(III) aminobenzyl-EDTA according to the method of Wang et al., J Immunol Meth. 18:157 (1977), which is incorporated herein by reference. Those hybridomas exhibiting high titer and relatively high affinity antibodies as determined by inhibition of binding by unlabelled antigen, were selected and injected intraperitoneally into BALB/c mice for ascites production. In the case of murine antibodies, the monoclonal anti-metal chelate antibodies were purified from mouse ascites by ion-exchange chromatography on DEAE-cellulose as described by Parham et al., J. Immunol Meth. 53:133 (1982), which is incorporated herein by reference.

The binding constants of the antibodies for the chelates were determined by the method of Eisen, Meth. Med. Res. 10:106 (1964), which is incorporated herein by reference. Briefly, the antibody and metal chelates were dialyzed to near equilibrium for 24 hours at 37° C. in 0.05 M 2-hydroyethyl-piperazine-ethanesulfonate (HEPES), 0.1 M NaCl, 0.1% NaN$_3$ and 0.1% bovine serum albumin at pH 7. The concentration of antibodybinding sites inside the dialysis bag was $10^{-7}$ M and the concentration of free In(III)-(L)-aminobenzyl EDTA complex was in the same range. CHA255 and CHB235 have affinities (binding constants) for In(III) EDTA complex on the order of $10^9$ L/M and $10^8$ L/M, respectively.

Chimeric anti-metal metal chelate antibodies can be produced expressing, for example, a variable region of murine origin and constant regions of human origin. To prepare such chimeric antibodies, DNA sequences of the variable and constant regions can be obtained from genomic DNA. Genomic DNA may be prepared and cloned by a variety of conventional techniques such as those described in Basic Methods in Molecular Biology, edited by L. G. Davis, M.D. Dibner and J. F. Battey, Elsevier, New York (1986); Feder, J., et al., AM. J. Hum. Genetics, 37:635-649 (1985); and Steffer, D and Weinberg, R. A., Cell, 15:1003-1010 (1978); Beidler et al., J. Immunol 141:4053-4060 (1988), which are incorporated herein by reference. For example, the DNA sequences encoding the desired variable light and heavy chain regions may be obtained from cellular DNA of a murine hybridoma expressing a desired anti-metal chelate antibody, while the DNA sequence encoding for the constant region may be derived from human lymphocytes, preferably human peripheral blood lymphocytes. Cellular DNA may be isolated by standard procedures, the genomic DNA fragmented into restriction fragments by restriction endonucleases, and the resulting fragments cloned into suitable recombinant DNA cloning vectors and screened with radiolabeled or enzymatically labeled probes for the presence of the desired DNA sequences. Methods for incorporating DNA constructs containing the desired sequences into cloning vectors and expression vectors are now well known in the art and described by numerous references such as Eukaryotic Viral Vectors, edited by Y. Gluzman, Cold Spring Harbor Laboratories publications, Cold Spring Harbor, New York (1982); Eukaryotic Transcription, edited by Y Gluzman, Cold Spring Harbor, New York (1985); Sequence Specificity in Transcription & Translation, edited by R. Calendar and L. Gold, Allan R. Liss, Inc., New York (1985); Maximizing Gene Expression, edited by W. Reznikoff and L. Gold, Butterworths, New York (1986); Mammalian Cell Technology, edited by W. G. Thilly, Butterworths, New York (1986); J. Sambrook and M. J. Gething, Focus (Bethesda Research Laboratories/Life Technologies, Inc.) 10 #3, pp. 41-48 (1988).

Appropriate host cells, preferably eukaryotic cells, may be transformed to incorporate the expression vectors by any one of several standard transfection procedures well known in the art, including, for example, electroporation techniques, protoplast fusion and calcium phosphate precipitation techniques. Such techniques are generally described by Toneguzzo, F et al., Mol and Cell Biol., 6:703-706 (1986); Chu, G. et al., Nucleic Acid Res., 15:1311-1325 (1987); Rice, D. et al., Proc Natl Acad Sci. USA, 79:7862-7865 (1979); and Oi, V., et al., Proc. Natl. Acad Sci USA, 80:825-829 (1983). Preferably, the recombinant expression vectors comprising the chimeric constructs are transfected sequentially into host cells. For example, the expression vectors comprising the chimeric light chain DNA constructs are first transfected into the host cells. Transformed host cells expressing the chimeric light chain polypeptides are then selected by standard procedures known in the art as described, for example, in Engvall, E. and Perlmann, P., Immunochemistry, 8:871-874 (1971). The expression vectors comprising the chimeric heavy chain DNA constructs are thereafter transfected into the selected host cells. Alternatively, both the chimeric light and heavy chain expression vectors can be introduced simultaneously into the host cells or both chimeric gene constructs can be combined on a single expression vector for transfection into cells. Following transfection and selection, standard assays are performed for the detection of chimeric antibodies directed against desired metal chelates.

The method of the present invention finds particular utility in separating bifunctional anti-metal chelate antibodies from the monofunctional anti-metal chelate antibodies. Bifunctional antibodies exhibiting one specificity against metal chelates and the other against a different antigen can be obtained. See, for example, U.S. Pat. No 4, 722,892, incorporating Ser. No. 367,784, U.S. Pat. No. 4,475,893 and Martinis et al., in PROTIDES OF THE BIOLOGICAL FLUIDS (H. Peters, ed.) pp. 311-316, Pergamon Press, Oxford (1983), which are incorporated herein by reference. For example, polydomas able to express bifunctional antibodies can be formed by fusing a cell secreting antibodies of the one specificity with a cell secreting antibodies of a different specificity. The heavy and light chains of the two antibodies then assemble to form a variety of antibody species including two active monofunctional, bivalent antibodies (corresponding to those of the parental cells), an active bifunctional antibody having one antigen-binding site comprising the light and heavy chain of one parent and the other antigen-binding site comprising the light and heavy chain of the other parent, and various other inactive species. The term "active" refers to constructs in which each antigen-binding site is composed of a light and a heavy chain from the same parent, thus giving it the parental specificity. "Inactive" refers to those constructs which lack the binding specificity of either parent because one or both antigen-binding sites comprise a heavy chain from one parent and a light chain from the other parent. The culture fluid from these polydomas contains various antibody species, including both the active monofunctional antibodies as well as active bifunctional antibodies.

Polyclonal anti-metal chelate antibodies can be obtained by means known to those skilled in the art. See, for example. Ghose. et al , Methods in Enzymology 93:326-327 (1883). Because such antiserum will contain a plurality of both anti-metal chelate antibodies and non-specific antibodies, the method of the present invention is of particular utility as it permits separation of anti-metal chelate antibodies from non-specific antibodies and proteins and allows identification of fractions enriched in anti-metal chelate antibodies. Such antiserum can contain anti-metal chelate antibodies having only low affinity for metal chelates whose retention time on oxo acid derivatized solid supports can overlap the retention time of other proteins found in the supernatant. The invention, therefore, is particularly suited to separate those antibodies having affinities for metal chelates of greater than $10^8$ L/M although it can also be used to separate those antibodies having affinities of $10^7$ L/M or even as low as $10^6$ L/M, from non-specific antibodies, although the resulting preparations may be accordingly less pure. The method is particularly well suited to preparing fractions having a high concentration of anti-metal chelate antibodies.

In accordance with the separation method of the present invention. a solution containing the anti-metal chelate antibodies, such as a cell culture supernatant, is dialyzed into a buffer solution. such as 50 mM sodium phosphate, pH 5.6, and applied to a column of an oxo acid derivatized resin which has been equilibrated in a starting solution. usually in the same buffer solution as that in which the antibody is applied. Buffers of pH between 3 through 8 can be used. Preferably. the resin is a sulfopropyl ion exchange resin. Examples of commercially available sulfopropyl resins include $SO_3$ conjugated particle (10 $\mu$m) with a 1000 angstrom pore size TOYO SODA TSK, SP 5-PW BioRad, Richmond. CA and LKB Pharmacia MONO-S or FFS, Pharmacia Fine Chemicals. Piscataway. NJ). Other oxo acid derivatized solid supports can be used. Appropriate oxo acids also include sulfates, phosphonates, phosphates and phosphate moieties. Appropriate support materials include polymeric resins, such as polystyrene and polyester, glass and glass matrices, dextran and cellulose, and polymer-coated supports although others will be known to those skilled in the art. The oxo acid can be conjugated to the solid support through means known to those skilled in the art. These oxo acids can be attached to resin through aliphatic, aromatic, or branched alkyls of varying length, provided that an oxo acid group is available.

In one embodiment of the invention, such as is appropriate for separating monoclonal anti metal chelate antibodies from non-specific antibodies and other non-specific proteins, bound material is eluted from the column using an elution solution with a linear gradient of increasing salt concentration, by means well known in the art. Various buffer salts can be used for this purpose including, but not limited to, sodium phosphate, sodium chloride and sodium acetate. Preferably, a linear gradient to 300 mM sodium phosphate, pH 5.6, is used Alternatively, sodium acetate buffer, pH 4.5, in conjunction with a sodium chloride gradient can be employed. Collected eluate fractions can be assayed for protein by means well known in the art, such as, for example, ultraviolet absorbance. Anti-metal chelate antibodies elute from the column at a later retention time than do non-specific antibodies, thereby permitting their separation.

An alternative embodiment as is appropriate for separating active bifunctional anti-metal chelate antibodies from other antibodies and proteins such as would be found in the culture of a polydoma. When the culture fluid is applied to the oxo acid derivatized solid phase support as described above and the eluants assayed for protein concentration, various peaks are evident. The bifunctional antibody will normally elute between the two parental types. The identity of the peak which corresponds to the active bifunctional can be determined by, for example, a modified ELISA requiring both activities to be present a single moiety. The elution conditions can then be selected so as to permit separation of the active bifunctional anti-metal chelate antibodies from the other antibodies species.

In a further embodiment, the invention provides a method for obtaining elution fractions enriched in anti-metal chelate antibodies from a polyclonal antiserum. When the antiserum is run on an oxo acid derivatized solid phase support, as described above, protein concentration approaches a Gaussian distribution. Anti-metal chelate activity, as determined by, for example, a quantitative ELISA determination, increases in the later eluting fractions. Thus, by running the antiserum on an oxo acid derivatized solid phase support and selecting later eluting material, anti-metal chelate antibodyenriched material will be obtained.

Although the invention is described in the following examples under particular conditions, including the identity of the solid support, the composition of the buffer, nature of the gradient, the affinity of the particular antibodies and so forth, it will be clear to one skilled in the art that the particular eluant conditions to be used to separate the desired antibody can be determined empirically. For example, using the teaching herein, an eluent condition may be found empirically in which non-specific antibodies will not be retained on oxo acid derivatized solid supports yet at which anti-metal chelate antibodies will be retained. The anti-metal chelate antibody can be removed from the oxo acid derivatized solid support by this same eluent having a salt concentration selected to discriminate between the two types of antibodies. The exact eluent conditions will depend on the type of derivatized support, eluent composition, and physical characteristics of both the anti-metal chelate antibodies and non-metal chelate antibodies being separated. The determination of appropriate elution conditions can then be applied to batch-mode purification, where the starting solution is chosen so as to prevent binding of non-specific proteins and the elution buffer chosen to elute the desired anti-metal chelate antibody The following examples are intended to illustrate but not limit the invention.

EXAMPLE I

HPLC Chromatography of Anti-Metal Chelate Antibodies

A sulfopropyl (SP) column (75×7.5 mm) was prepared using $SO_3$ conjugated particle (10 $\mu$m) with a 1000 angstrom pore size TSK-SP-5-PW, BioRad Richmond, CA) according to the manufacturer's instructions and equilibrated in 50 mM sodium phosphate buffer, pH 5.6. Approximately 3 mg of the anti-metal chelate antibody, XCHA351, was dialyzed against 50 mM sodium phosphate, pH 5.6, overnight. 1 2 mg of antibody was loaded onto the column and allowed to bind to the matrix. The antibody was eluted from the column using combinations of Buffer A (50 mM sodium phosphate pH 5.6) and Buffer B (0.3 M sodium phosphate pH 5 6) to give a linear gradient of increasing salt from 50 mM to 0.18 M sodium phosphate, pH 5.6, at a rate of 1 ml/minute over a period of 60 minutes. Eluate fractions were collected and the presence of antibody determined by absorbance at 283 nm using an IBM 9563 variable wavelength ultraviolet detector The retention time of XCH351 was 60 716 minutes.

EXAMPLE II

Separation of Anti-metal Chelate Antibodies from Non-specific Antibodies 1.2 of XCHA351 and XCEM449 08, a non-specific antibody, were mixed and chromatographed together on a sulfopropyl column according to procedures of Example I. The two antibodies exhibited retention times of 60.716 and 34.458 minutes, respectively, as shown in FIG. 1(a), which were equivalent to approximately 156 mM sodium phosphate and 99 mM sodium phosphate. The retention time of the later peak was comparable to XCHA351 in Example I, indicating the identity of the antibodies. The anti-metal chelate antibody, therefore, had a considerably longer retention time on the SP column than the non-specific antibody, despite XCHA351 having a pI of 8.5 versus 8.8 for XCEM449.08.

EXAMPLE III

Effect of Hapten on Anti-metal Chelate Antibody and Non-specific Antibody

XCHA351 and XCEM449.08 were prepared and run together on a sulfopropyl column as in Examples I and II with the following modifications. 2.5 mL of 200 mM Co/EDTA was added to 500 mL of each of Buffers A and B, to a final concentration of 1 mM. Each antibody was preincubated with a molar excess of 45:1 hapten to antibody for 3 hours at room temperature before being loaded onto the column.

Figure 1B:
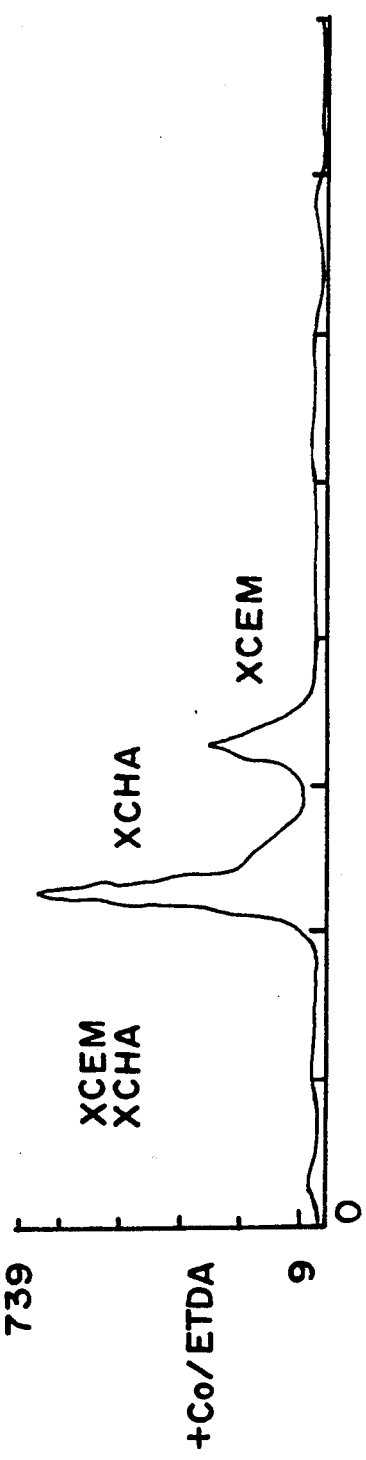

The retention time of XCEM449.08 was 32.673 minutes (95 mM sodium phosphate) and that of XCHA351 was 22.466 minutes (73 mM sodium phosphate) as shown in FIG. 1(b). Therefore, the binding of the antimetal chelate antibody was considerably inhibited in the presence of hapten while that of the non-specific antibody was not. This result indicates XCHA351 binds to the column at or near its antigen-binding site.

EXAMPLE IV

Separation of Other Antibodies

The following additional antibodies were chromatographed and their elution patterns analyzed as described in Example I, in the presence or absence of metal chelate hapten CHB235, XCHA351, CYA339.4, CEV MSC and ECH037. The results are presented in Table II.

TABLE II

SHARED CHARACTERISTICS OF ANTIBODIES

| Antibody | pI | Specificity | Characteristics | Elution salt concentration (mM sodium phosphate pH 5.6) |
|---|---|---|---|---|
| CHA255 | 7.5 | $^{111}$In metal chelate | murine monoclonal monofunctional | 160-175 mM |
| CHB235 | 6.6-7.2 | $^{111}$In metal chelate | murine monoclonal monofunctional | 290 mM |
| XCHA351 | 8.5 | $^{111}$In metal chelate | chimeric monoclonal monofunctional | 160-175 mM |
| XCEM449.08 | 8.8 | tumor CEA | chimeric monoclonal monofunctional | 100 mM |
| CYA339 | | $^{90}$Y metal chelate | murine monoclonal monofunctional | 300 mM |
| CEVMSC | 7.0-7.5 | tumor CEA | murine monoclonal monofunctional | 115 mM |
| ECH037 | | $^{111}$In metal chelate/ tumor CEA | murine polydoma produced bifunctional | 145 mM |
| *BxBFA | 8.6 | $^{111}$In metal chelate/ tumor CEA | chimeric monoclonal bifunctional | 140 mM |
| pCYA | | Y-metal chelate | murine polyclonal monofunctional | |

*See Example V for conditions

In all experiments, the anti-metal chelate antibodies showed extended retention times on the SP column, as compared with non-specific antibodies, in the absence of hapten. Moreover, retention times were similar for murine antibodies and their chimeric derivatives despite the fact that the murine antibodies have a such lower pI than do the chimerics. See for example, CHA255 and XCHA351 However, the retention time of anti-metal chelate antibodies in the presence of the hapten analog, 1 mM Co/EDTA, was dramatically reduced as compared to only slight changes with the non-specific antibodies. This longer retention time of anti-metal chelate antibodies and its abrogation in the presence of metal chelate hapten indicate that the binding of these antibodies to sulfopropyl resin reflects interaction in the antigen reactive binding region.

EXAMPLE V

Separation of Antibodies From Culture Fluid

The culture fluid from a hybridoma expressing IgG from XCEM449.08 and XCHA351 was chromatographed as described in Example with the following modifications. 20 ml of hybridoma culture fluid was concentrated to 3 mls and the buffer changed to PBS (10 mM sodium phosphate, pH 7.2, 150 mM sodium chloride) by diafiltration. Carboxypeptidase B was added to 0.1% of total protein and allowed to incubate for ½ hour at 22° C. The fluid was then dialyzed for 18 hours against 50 mM sodium phosphate, pH 5.60, before filtration through 0.2 μm membrane filter (ACRODISC filter, Gelman, Ann Arbor, MI). It was then loaded onto the column by HPLC with a 10 ml sample loop. Buffer A was run over the column until the absorbance at 283 nm reached baseline. The gradient elution then proceeded as in Example I.

Six protein peaks were obtained corresponding to the six species of antibodies present. The identities of the peaks were determined by a modified ELISA procedure which required both activities to be present on the same antibody. The active bifunctional BXBFA eluted as peak two with a retention time of about 40 minutes, compared to about 30 minutes for XCEM449.08 and about 60 minutes for XCHA351. The actual retention times were as follows: XCEM449.08: 28.637 minutes, BXBFA: 40.885 minutes and XCHA351: 57.740 minutes. Therefore the method can be used to separate the bifunctional antibodies, which exhibit one metal binding site, from the parent antibodies, which exhibit either no metal chelate binding sites or two metal chelate binding sites.

EXAMPLE VI

Preparation of Metal Chelate Immunogen

Conjugation of (L)-isothiocyanate benzyldiethylenetriaminepentaacetic acid (ITSBD) containing yttrium (Y) with thyroglobulin was performed as follows. Initially, 45 µl of 112 mM ITCBD in 0.3 N HCl, 60 µl of 0.1 M $YCl_3$ and 25 µCi of $^{90}Y(III)$ were mixed and incubated for 15 minutes at room temperature. The pH of the solution measured between 0 and 1. Following incubation, 50 µl of 1 M $NaHCO_3$ was added to the labeling solution in 10 µl increments until neutral pH was reached. Thin layer chromatography of the sample using methanol:ammonium hydroxide::4:1 as the solvent revealed that 91% of the radioactivity was present as $^{90}Y$-ITCBD. The $^{90}Y$-ITCBD was added to 0.3 ml thyroglobulin (19 mg/ml) in borate buffered saline (BBS), pH 10. The reaction proceeded at 37° C. for 90 minutes with stirring, followed by thin layer chromatography which revealed that 60% of the activity moved with the solvent. Excess reagents were removed on a 15 ml desalting column comprising 90-180 µm beads which fractionates in the 1000-6000 dalton range P6 column, BioRad, Richmond, CA) equilibrated with PBS, pH 7.2. The protein fraction was eluted with PBS, collected and filtered through 0.2 µ membrane filter (ACRODISC Filter, Gelman, Ann Arbor, MI). Protein content was measured by Coomassie Blue.

Conjugation of Y-ITCBD with BSA was performed in a similar manner. After $^{90}Y$-ITCBD was prepared as described above, 200 ml of 60 mg/ml BSA and 10 µl saturated $Na_2CO_3$ were added and incubated for 1 hour at 37° C. Thin layer chromatography showed 12.9% free $^{90}Y$-ITCBD Excess reagents were removed and protein concentration determined as described above.

Assay for Bifunctional Activity of Bifunctional Chimeric Antibody CEM/CHA

Polystyrene beads are coated with monoclonal antibody CEV124, which specifically binds CEA. Such beads are available in the immunoradiometric assay kit for the measurement of carcinoembryonic antigen (TANDEM CEA-R kit sold by Hybritech Incorporated, San Diego, California). CEA is then added to the coated beads and allowed to incubate for one hour at 37° C., then the beads are rinsed with PBS. Supernatant containing bifunctional chimeric CEM/CHA is then added to the beads, and the reaction is allowed to proceed for one hour at 37° C. After a rinse with PBS, the beads are mixed with an $^{111}In$-EDTA complex as described in Reardan et al., supra, or $^{111}In$-loaded EOTUBE, (the synthesis of which is described below) for one hour at 37° C. After another rinse, immune complexes comprising antibody CEM/CHA are collected onto paper filters which were counted in a gamma counter.

The synthesis of EOTUBE and its use in a standard Scatchard are as follows. EOTUBE is EDTA substituted at one of the internal ethylene carbons (S stereochemistry at that substituted carbon) through the benzylic carbon of an N-(2-hydroxyethyl)-N'-(p-benzyl)thiourea moiety. The synthesis of EOTUBE was performed excluding metal ions as much as possible. (For example, all glassware was washed with 6M HCl, and only deionized water was used).

(S)-p-nitrobenzyl EDTA was prepared and converted to (S)-4-isothiocyanatobenzyl EDTA (hereinafter abbreviated as ITCBE) as described on U.S. Pat. No. 4,622,420, and Meares, C. F., *Anal. Biochem* 142: 68-75 (1984), which the lyophilized ITCBE was resuspended in 0.3 M HCl (Ultrex, J. T. Laker, Phillipsburg, N.J.) to a final concentration of roughly 50 mM. This solution was stored at $-70°$ C. Unless indicted otherwise, all reactions were done in aqueous solution at 40° C.

2.5 ml of 20 mM ITCBE was added to 1.35 ml of 200 mM ethanolamine and the pH adjusted to 11.0 with 10 N NaOH. The volume was adjusted to 5 ml with water and the mixture allowed to react for 15 minutes, at which time it was checked by HPLC analysis. All of the ITCBE was converted to EOTUBE, with a retention time of 3.6 minutes on a HPLC (C18 reverse phase column comprising 18 carbons per chain, eluted with a linear gradient of aqueous buffer of 50 mM triethylammonium acetate to neat methanol on a Hewlett-Packard 1090 instrument).

The product was purified by anion exchange chromatography on an 11 ml column of diethylaminoethyl Anion exchange resin DEAE SEPHADEX (Pharmcia Fine Chemicals, Piscataway, N.J.) A-25, eluted with a 110 ml gradient of 0.1 to 1 M ammonium formate, pH 6. (The column was monitored at 280 nm.) Fractions containing the product were pooled and lyophilized. The product had an absorbance maximum at 246 nm with an extinction coefficient of 18000.

The structure was purified by carbon 13 NMR spectroscopy (on a Varian Instruments Model XL-300 300 Mhz instrument. The spectrum was run with deuterated water.) The peak corresponding to the carbon in the isothiocyanate moiety in ITCBE was at 139 ppm, and was replaced by a peak at 182 ppm in EOTUBE. This peak corresponds to the carbon in the thiourea linkage. The aromatic region (128-138 ppm) of the spectrum of ITCBE shows four peaks, while that of EOTUBE shows three. In the aliphatic region, there are five peaks in common for ITCBE and EOTUBE, and an additional two peaks at 64 and 49 ppm in the EOTUBE spectrum. The latter peaks correspond to the carbons adjacent to the hydroxyl and thiourea moieties, respectively.

EXAMPLE VII

Production of polyclonal antisera

Polyclonal antisera to Y-ITCBD were prepared in A/J and BALB/c mice. Mice were injected intraperitoneally (i.p.) with 100 µg $^{90}Y$-ITCBD-thyroglobulin in either complete Freund's adjuvant (CFA) or alum precipitate at day 0. At day 14, mice were reinjected with 50 µg of the same antigen. Those animals receiving CFA initially received incomplete Freund's adjuvant (IFA) with the second boost, while the other mice were injected with the same alum precipitate. The mice were bled on day 21 and serum anti-Y-ITCBD levels were measured by ELISA, using Y-ITCBD-BSA as the antigen.

EXAMPLE VIII

Separation of anit-metal chelate antibodies from polyclonal antiserum

The polyclonal anti-Y-ITCBD serum diluted into 50 mM sodium phosphate, pH 5.6, was chromatographed on an SP column as described in Example I. IgG fractions were analyzed by ELISA by binding to Y-ITCBD-BSA, using a specific antibody CYA 339, as a positive control. The OD from ELISA was normalized to the mV reading for each fraction and compared to time. As shown in Table III, the amount of Y-ITCBD reactive antibodies increases with retention time on the SP column. The Y-ITCBD reactive antibodies were retained longer on the column than most other antibodies, as was the case for the monoclonal antibodies to In-ITCBE.

TABLE III

| Fraction time (minutes) | ELISA OD490 average | mV | Normalized ELISA OD 1000 · (OD490/mV) |
|---|---|---|---|
| 11 | 0.005 | 18.1 | 0.276 |
| 15 | 0.013 | 56 | 0.232 |
| 20 | 0.070 | 122.5 | 0.571 |
| 25 | 0.238 | 162.8 | 1.462 |
| 30 | 0.401 | 170.7 | 2.349 |
| 35 | 0.603 | 159.5 | 3.781 |
| 40 | 0.589 | 145.0 | 4.062 |
| 45 | 0.809 | 123.4 | 6.556 |
| 50 | 0.582 | 99.1 | 5.994 |
| 55 | 0.547 | 95.2 | 5.746 |
| 60 | 0.577 | 88.9 | 6.490 |
| 65 | 0.818 | 81.7 | 10.012 |
| 70 | 0.805 | 92.5 | 8.703 |
| 75 | 1.758 | 111.9 | 15.711 |
| 80 | 1.247 | 81.2 | 15.357 |
| 85 | 0.573 | 51.5 | 11.126 |
| 90 | 0.402 | 39.8 | 10.101 |

EXAMPLE IX

Reduction of CHA255 F(ab')$_2$ and separation on SP column

CHA255 (F(ab')$_2$ was generated by enzymatic cleavage using pepsin. Briefly, pepsin and the antibody were each dissolved separately in 0.1 M sodium citrate, pH 3.9, and then mixed and incubated at a concentration of 25 units pepsin/mg antibody at 37° C. overnight. This left a divalent F(ab')$_2$ piece with antibody activity and small peptides from the Fc region.

To each of 2 tubes, 250 μl of (3 mg) CHA255 F(ab')$_2$ in 0.1 M sodium phosphate, pH 7.0, 0.2 M (NH$_4$)SO$_4$ and 50 μl of 60 mM cysteine in 2 M Tris.HCl pH 8 2, was added and incubated for 3 hours at 37° C. To one tube, 50 μl of 0.18 M Br(CH$_2$)$_2$NH$_2$ added and to the other 50 μl 0.18 M ICH$_2$COOH. Both tubes were incubated at 21° C. for 1 hour in the dark. The Br(CH$_2$)$_2$NH$_2$alkylated CHA255 Fab' was added to 5 ml of 50 mM sodium phosphate, pH 5.6 and the IC$_2$-COOH alkylated CHA255 Fab, to 5 ml of 50 mM sodium phosphate, pH 5.6. Each was dialyzed against L of 50 mM sodium phosphate, pH 5.6. The samples were run over SP columns as described in Example I, except that a linear gradient of 50 mM to 300 mM sodium phosphate, pH 5.6, was run over 100 minutes and was detected at 280 nm.

Cysteine reduction of disulfide bonds between the two heavy chains generated Fab', although some F(ab')$_2$ remained. The retention time for Fab' was 32.9 minutes compared to 69.3 minutes for F(ab')$_2$ when either alkylating reagent was used suggesting that the SP column is not interacting with the extra charges created by alkylation of broken disulfide bonds. The identity of the peaks was confirmed by SDS gel electrophoresis. The retention time for intact XCHA351 under these gradient conditions is also about 69 minutes. Therefore, these results indicate that CHA255-derived antibodies bind to the SP column through their Fab regions and that avidity affects the binding of fragments as well as of intact antibodies.

Although the invention has been described in terms of the presently preferred embodiments, it will be apparent to one skilled in the art that modifications can be made without departing from the spirit of the invention. Thus, the invention is limited only by the following claims.

We claim:

1. A method for obtaining eluant fractions enriched in anti-metal chelate antibodies from a preparation containing said anti-metal chelate antibodies and non-specific proteins, comprising the steps of:
   a. applying said preparation to a sulfopropyl derivatized solid support equilibrated in a starting solution;
   b. adding an elution solution containing a salt in a concentration sufficient to elute non-specific proteins from said support;
   c. adding a further elution solution containing a salt in an increased concentration sufficient to eluate said anti-chelate antibodies from said support; and
   d. collecting the eluant fraction released in step c.

2. The method of claim 1 wherein said solid support is selected from the group consisting of polymer-coated supports, polystyrene, polyester, glass, dextran and cellulose.

3. The method of claim 1 wherein said salt is selected from the group consisting of sodium phosphate, sodium chloride and sodium acetate.

4. The method of claim 1 wherein said anti-metal chelate antibody is a fragment bearing the antigen reactive region.

5. The method of claim 1 wherein said applying step is performed in starting solution of sufficient salt concentration to prevent binding of a portion of said non-specific proteins without preventing binding of said anti-metal chelate antibodies.

6. A method of separating bifunctional anti-metal chelate antibodies from a preparation containing said bifunctional anti-metal chelate antibodies, and monofunctional anti-metal chelate antibodies and non-specific antibodies, comprising the steps of:
   a. applying said preparation to a sulfopropyl derivatized solid support in a starting solution;
   b. adding an elution solution containing a salt in a concentration sufficient to elute non-specific antibodies from said support without detaching said bifunctional anti-metal chelate antibodies and said monofunctional anti-metal chelate antibodies;
   c. adding a further elution solution containing a salt in an increased concentration sufficient to eluate said bifunctional anti-metal chelate antibodies from said support but not elute said monofunctional anti-metal chelate antibodies from said support; and
   d. collecting the eluant containing said bifunctional anti-metal chelate antibodies eluted in step c.

7. The method of claim 6 wherein said solid support is selected from the group consisting of polymer-coated supports, polystyrene, polyester, glass, dextran and cellulose.

8. The method of claim 6 wherein said salt is selected from the group consisting of sodium phosphate, sodium chloride and sodium acetate.

9. The method of claim 6 wherein said anti-metal chelate antibody is a fragment bearing the antigen reactive region.

10. The method of claim 6 wherein said applying step is performed in starting solution of sufficient salt concentration to prevent binding of a portion of said non-specific antibodies without preventing binding of said bifunctional anti-metal chelate antibodies.

11. A method for separating anti-metal chelate monoclonal antibodies from non-specific proteins, comprising the steps of:
   a. applying said preparation to a sulfopropyl derivatized solid support equilibrated in a starting solution;
   b. adding an elution solution containing a salt in a concentration sufficient to elute non-specific proteins from said solid support without releasing the anti-metal chelate antibodies.
   c. adding a further elution solution containing a salt in an increased concentration sufficient to eluate the anti-metal chelate monoclonal antibodies from said solid support; and
   d. collecting the eluant containing anti-metal chelate monoclonal antibodies eluted in step c.

12. The method of claim 11 wherein said solid support is selected from the group consisting of polymer-coated supports polystyrene, polyester, glass, dextran and cellulose.

13. The method of claim 11 wherein said salt is selected from the group consisting of sodium phosphate, sodium chloride and sodium acetate.

14. The method of claim 11 wherein said anti-metal chelate antibody is a fragment bearing the antigen reactive region.

15. The method of claim 11 wherein said applying step is performed in starting solution of sufficient salt concentration to prevent binding of a portion of said non-specific proteins without preventing binding of said anti-metal chelate antibodies.

16. A method for separating anti-metal chelate antibodies from non-specific proteins in a preparation, comprising the steps of:
   a. applying said preparation to a sulfopropyl derivatized solid support equilibrated in a starting solution;
   b. adding an elution solution containing a salt in a concentration sufficient to elute those non-specific proteins which eluate at a concentration lower than do anti-metal chelate antibodies, but not sufficient to elute said anti-metal chelate antibodies;
   c. adding a further elution solution containing a salt in an increased concentration sufficient to eluate said anti-metal chelate antibodies, but not sufficient to elute non-specific proteins having an elution salt concentration higher than said anti-metal chelate antibodies; and
   d. collecting the eluant containing said anti-metal chelate antibodies eluted in step c.

17. The method of claim 16 wherein said solid support is selected from the group consisting of polymer-coated supports, polystyrene, polyester, glass, dextran and cellulose.

18. The method of claim 16 wherein said salt is selected from the group consisting of sodium phosphate, sodium chloride and sodium acetate.

19. The method of claim 16 wherein said anti-metal chelate antibody is a fragment bearing the antigen reactive region.

20. The method of claim 16 wherein said applying step is performed in a starting solution of sufficient salt concentration to prevent binding of said non-specific proteins having an elution salt concentration on said oxo acid derivatized solid support lower than that of said anti-metal chelate antibodies but not sufficient to prevent binding of said anti-metal chelate antibodies.

21. A method of separating anti-metal chelate antibodies from non-specific proteins in a preparation, comprising the steps of:
   a. applying said preparation to a sulfopropyl derivatized solid support;
   b. removing material not bound to said oxo acid derivatized solid support;
   c. adding an elution solution containing a metal chelate or analog reactive with said anti-metal chelate antibodies thereof to said oxo said derivatized solid support; and
   d. collecting the eluant containing said anti-metal chelate antibody eluted in step c.

22. The method of claim 21 wherein said solid support is selected from the group consisting of polymer-coated supports, polystyrene, polyester, glass, dextran and cellulose.

23. The method of claim 21 wherein said salt is selected from the group consisting of sodium phosphate, sodium chloride and sodium acetate.

24. The method of claim 21 wherein said anti-metal chelate antibody is a fragment bearing the antigen reactive region.

* * * * *